United States Patent [19]
Demorest

[11] Patent Number: 5,372,695
[45] Date of Patent: Dec. 13, 1994

[54] APPLICATION SPECIFIC CAPILLARY ELECTROPHORESIS

[75] Inventor: David M. Demorest, Scotts Valley, Calif.

[73] Assignee: Applied Biosystems, Inc., Foster City, Calif.

[21] Appl. No.: 59,946

[22] Filed: May 7, 1993

[51] Int. Cl.⁵ .............................................. B01D 61/42
[52] U.S. Cl. .............................................. 204/299 R
[58] Field of Search ..................... 204/299 R, 108.1; 422/63

[56] References Cited

U.S. PATENT DOCUMENTS 5,180,475  1/1993  Young et al. ................... 204/299 R

*Primary Examiner*—John Niebling
*Assistant Examiner*—Edna Wong
*Attorney, Agent, or Firm*—Donald R. Boys

[57] ABSTRACT

A capillary electrophoresis system incorporates an application specific cassette having run buffers and capillary column selected for the specific separation procedure, with buffer reservoirs sealed for storage and shipment. A serving apparatus is provided to accept the cassette and perform the specific electrophoresis procedure until buffer is depleted or the performance of the separation column deteriorates. The serving apparatus comprises liquid transfer apparatus, removable covers for the reservoirs of the cassette, electrodes for establishing voltage potential, and a control system.

19 Claims, 8 Drawing Sheets

APPLICATION SPECIFIC CAPILLARY ELECTROPHORESIS

FIELD OF THE INVENTION

This invention is in the field of apparatus and methods for separating macromolecules by capillary electrophoresis, and pertains in particular to high-performance automated apparatus and methods.

BACKGROUND OF THE INVENTION

There has been rapid growth in recent years in apparatus and methodology for biochemical enterprise, particularly for cleavage, separation and analysis of macromolecules such as DNA, including human DNA. There are a number of uses, such as determining the presence of genetically induced conditions such as Sickle-Cell Anemia, Huntington's Chorea, and others. Fluorescent gel scanning has also become important as an identification tool. Genetic code from a human hair or a flake of skin can be matched to a single human being, supplementing older procedures, such as fingerprint analysis in criminal law.

Macromolecules are typically separated and identified by electrophoresis. In electrophoretic separation electrically charged macromolecules of different size and structure move at different velocities in a specific medium under the influence of an electrical field. Typical mediums and geometries in use include agarose slabs, polyacrylamide gel films, matrix-filled columns, and micro columns (capillary tubings) either with or without a gel matrix.

The use of micro-column, (capillary) electrophoresis for macromolecule separation and analysis is a relatively more recent development than slab and film techniques. A principle advantage of micro-column techniques is their suitability for analysis of very small sample volumes, e.g. microliter or sub-microliter amounts of sample. Being able to analyze such small amount of sample has become very important because, oftentimes, the available volume of sample for analysis is extremely small. For example, in forensic and criminal investigations, the only material that may be available for analysis may comprise a fingernail scraping or a stain on an article of clothing.

Another advantage of microcolumn techniques is that the relatively smaller and simpler apparatus lends itself to techniques of automation more readily than do slab and film systems. For example, a detector to monitor bands passing a point in a micro-column is a relatively simple device compared to a scanning detector for monitoring a plurality of channels in an agarose slab. The column itself is small and easier to manipulate. The reservoirs for storing buffers and other solutions are smaller as well and more easily managed. There are many other examples of the advantages of microcolumn electrophoresis.

With all of the advantages and advances in electrophoresis by the use of micro-columns, there remain problems that have not been solved before the present invention. Many of these are simply variations of difficulties encountered in the effort to automate all types of electrophoresis apparatus. For example, considering only capillary electrophoresis, not all starting samples respond in the same way to the same set of electrophoretic circumstances. By circumstances is meant the value set of all of the variables that effect electrophoresis of sample material.

The variable set includes the length and bore of the capillary, the separation matrix in the column, the electrical potential maintained across the ends of the column, the types of buffers used, the geometry of the physical apparatus, the arrangement and techniques for sample injection, ability to control temperature and to dissipate heat generated in the electrophoresis operations, arrangements for fraction collection and more.

Variable sets for specific samples and purposes have been developed empirically over time and tested. New circumstances for new sample compositions continue to be developed.

Some circumstances are relatively easy to manage. For example, the electrical potential across the ends of a column. Others are quite difficult. The only way to change the capillary bore, for example, is to change the capillary, and to do so is a relatively clumsy operation in many existing systems.

What is clearly needed is an apparatus wherein the circumstances difficult to change are incorporated into a module that can be placed in a serving apparatus to provide the circumstances more generic and relatively easier to manage. In this invention, the module would provide circumstances specific to a pretested specification, for separations of a certain type and class of sample. The module, which is called an application-specific cassette by the inventors, includes a support block, or framework, designed to interface physically to the serving apparatus; a capillary of the correct length, bore, material, and wall thickness, and incorporating a particular gel or liquid matrix; buffers solutions at the ends of the capillary; and one or more reservoirs for liquids needed in the specific procedure. In a specific and preferred embodiment of the present invention, the application-specific cassette is disposable. When the buffers are depleted, the matrix ages and deteriorates, or any other change renders the cassette unusable, the cassette is simply removed, and a new one substituted to the serving apparatus.

The serving apparatus includes a robotic system with a liquid-handling apparatus having a probe translatable in three dimensions, and an electrode in contact with fluid in the liquid handling apparatus.

SUMMARY OF THE INVENTION

In an embodiment of the invention an application-specific cassette is provided for performing a particular electrophoresis procedure. The cassette comprises an inlet buffer reservoir with an upper opening and a first run buffer selected for the specific procedure, an outlet buffer reservoir spaced apart from the inlet buffer reservoir and with an upper opening and a second run buffer selected for the specific procedure, and a capillary electrophoresis column opening at one end into the inlet buffer reservoir below the surface of the first run buffer and opening at the other end into the outlet buffer reservoir below the surface of the second run buffer. Removable seal means are provided to seal the upper openings of the reservoirs for storage and shipment before use.

In a preferred embodiment, the buffer reservoirs are formed into an injection molded cassette with the column mounted horizontally and sealed through a sidewall of each of the buffer reservoirs. A preferred means of sealing the reservoirs before use is by a liquid-impervious film placed over the reservoir openings with an adhesive. There may also be auxiliary reservoirs formed into the cassette for reagents and buffers specific to the specific application.

A serving apparatus is provided to accept the cassette and perform the specific procedure until buffers are depleted or the column performance deteriorates. The serving apparatus has a probe with a tip and pumping means for withdrawing and dispensing liquids to and from reservoirs, a translation sub-system for moving the tip into and out of liquids in reservoirs, cover assemblies for engaging openings in the reservoirs and inserting an electrode and a waste tube in the reservoirs, and a high voltage power supply for providing electrical potential selectively and independently to each of the buffers, There is in addition an electrode in the liquid transfer apparatus providing an ability to sample injection and fraction collection by electromigration, and a detector interface to detect separated bands in the capillary column may be provided in some embodiments.

A system is provided for electrophoresis comprising a serving apparatus as described and an application specific cassette, and in an alternative embodiment, the application-specific cassette is configured with an intermediate buffer reservoir and two capillary columns, to perform post-separation detection.

DESCRIPTION OF THE PREFERRED EMBODIMENTS

Figure 1A:
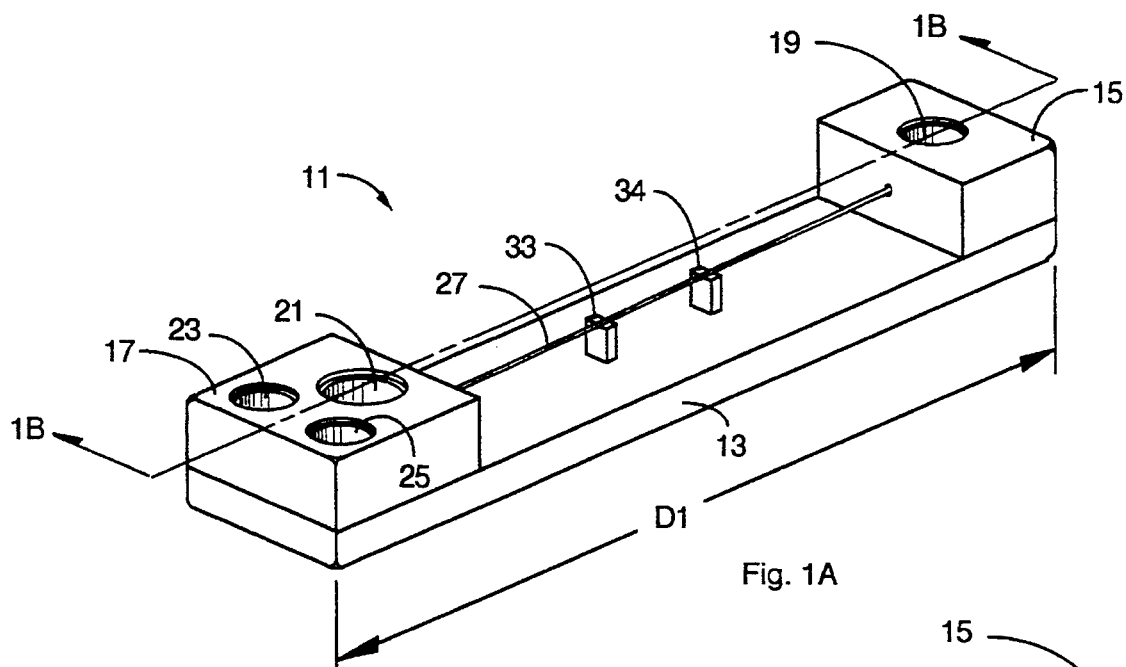
FIG. 1A is an isometric view of an application-specific cassette 11 according to an embodiment the present invention.

FIG. 1A is an isometric view of an application-specific cassette 11 according to an embodiment of the present invention. In this embodiment a base block 13 establishes the overall length D1 of the cassette, and end blocks 15 and 17 are securely fastened, such as by adhesive material, to the base block. Inlet and outlet buffer reservoirs 19 and 21 are machined into end blocks 15 and 17 respectively, and auxiliary solution reservoirs 23 and 25 are provided in end block 17.

It will be apparent to one with skill in the art that the choice of inlet and outlet for the buffer reservoirs is arbitrary and interchangeable, and the placement of the auxiliary reservoirs is also arbitrary. They could as well be placed in the block at the opposite end of the cassette, or divided between the blocks. Also, the use of auxiliary reservoirs in a cassette is optional, rather than necessary to the invention. The use of one or more auxiliary reservoirs provides a preferable feature of extending the useful life of the cassette.

There are a number of different suitable materials for the blocks. They may be phenolic, polycarbonate, or one of several other polymeric materials available that are machinable and relatively impervious to the chemicals and sample material used in micro-column electrophoresis, and non-contaminating to the electrophoresis chemistry. Moreover, the assembly need not be from separate blocks as shown. The cassette might be formed in a single piece by processes such as injection molding, or machined from a single piece. In the present embodiment, one of the main criteria is cost, and in a preferred embodiment the cassette is meant to be a disposable entity after use.

Figure 1B:
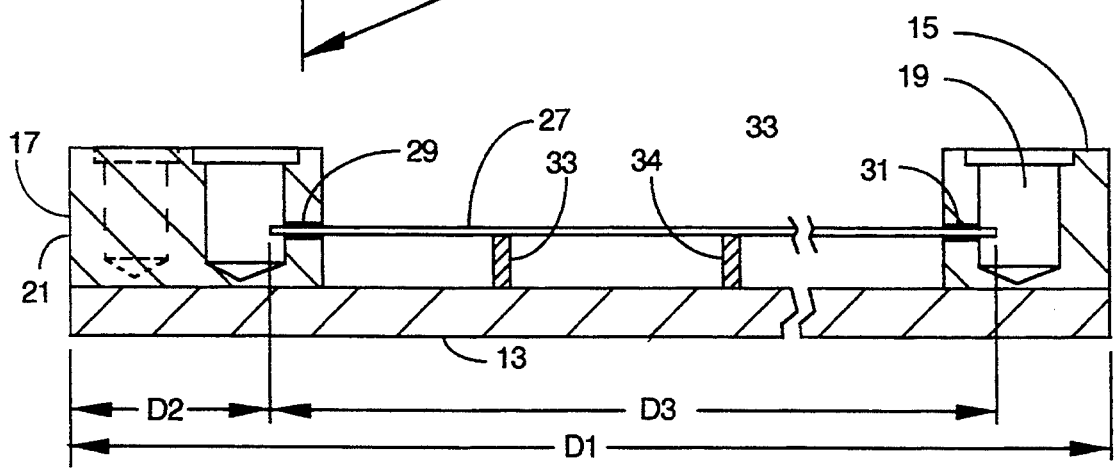
FIG. 1B is a cross-section of cassette 11 along section line 1B—1B of FIG. 1A.

In addition to the provision of the several reservoirs, the block is prepared in this embodiment to mount a capillary tubing 27 between inlet and outlet buffer reservoirs 19 and 21. FIG. 1B is a section view of block 13 of FIG. 1A taken along line 1B—1B. Capillary tubing 27 is shown mounted through a bore 29 into buffer reservoir 21 and through a bore 31 into buffer reservoir 19. The capillary in this embodiment is permanently mounted by means of a thermosetting adhesive, or other suitable adhesive material compatible with the material of the blocks.

The position of the ends of the capillary relative to the position of the buffer reservoirs, as may be determined by the capillary length D3 and dimension D2, is carefully maintained to a predetermined position, for reasons of transfer of materials, which will be apparent in following descriptions.

Two capillary supports 33 and 34 (FIG. 1A and 1B), comprising blocks each having a groove to support the capillary, are provided adhered to base block 13. Capillary 27 is adhered in this embodiment to supports 33 and 34 by a suitable adhesive, not shown in the figure. If the capillary is produced with an opaque coating on the outer diameter, as is the case with many capillary tubings in the art, this coating is removed between supports 33 and 34, to provide a clear area for a detector to be described below.

As was described in the background section above, workable sets of circumstances for different applications for electrophoresis have been empirically developed. An application-specific cassette according to the present invention is provided for a specific known solution, and comprises therefore a gel or liquid matrix in the capillary, buffer solutions in the inlet and outlet buffer reservoirs, and optionally auxiliary chemicals in the auxiliary reservoirs. Additional buffer may also be provided in one or both of the auxiliary reservoirs, so fresh buffer solution may be transferred at some time in operation from an auxiliary reservoir to one or both of the buffer reservoirs.

In the present embodiment, after a cassette is assembled, the capillary is sealed into place, and buffers and other chemicals are placed in the various reservoirs, the top of each reservoir is sealed with a foil treated paper seal having an adhesive. This seal is similar to seals of this sort used for pharmaceuticals, over-the-counter medicines and many other consumer items. The result is a cassette complete with capillary and run buffers that may be manufactured economically in quantity and stored for a considerable time before use. Cassettes may be thusly provided as a product to users having serving apparatus. New variations may also be provided as new specific chemistries are developed.

It will be apparent to those with skill in the art that the various dimensions of a cassette within the scope of the present invention may vary widely. For example, capillary bore may vary according to specific application, ranging from perhaps 10 to as much as 100 micrometers. Also, the length of a capillary can vary, depending on the length of a cassette, which may be designed to fit one or another of various serving apparatus, and on other factors as well. The length of a capillary can vary from as short as 1 cm. to as long as 50 cm., or even longer in some applications.

Although it is not readily apparent in the drawing figures, which are not meant to present dimensions to scale, there is an advantage in keeping the buffer reservoirs rather small, and the auxiliary reservoirs relatively large. Typical buffer reservoirs range from 0.1 to 10 milliliters. A relatively small buffer reservoir saves time in procedures for purging and replacing buffer solution in operation. A relatively large auxiliary reservoir provides relatively more material for use in operation, extending the period between necessary service procedures. Accordingly, in the present embodiment, the buffer reservoirs are much smaller than the auxiliary reservoirs.

Figure 1C:
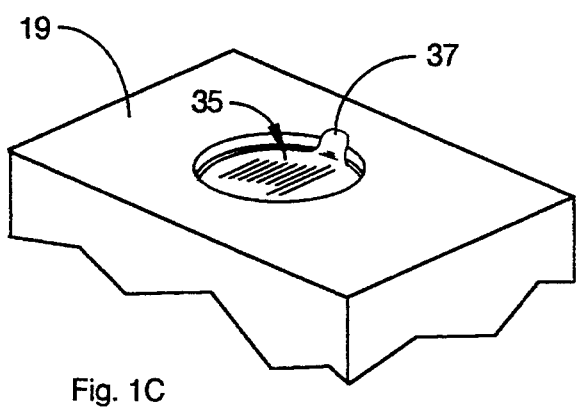
FIG. 1C is an isometric view of one buffer reservoir of a cassette showing a seal film.

FIG. 1C is an isometric view, enlarged, of block 15 from FIG. 1A, showing an exemplary seal 35 covering reservoir 19. A tab extension 37 from the foil seal in this embodiment allows a user to grasp and peel the seal from the top of the reservoirs when mounting the cassette to a serving apparatus for use, as described below.

Figure 2A:
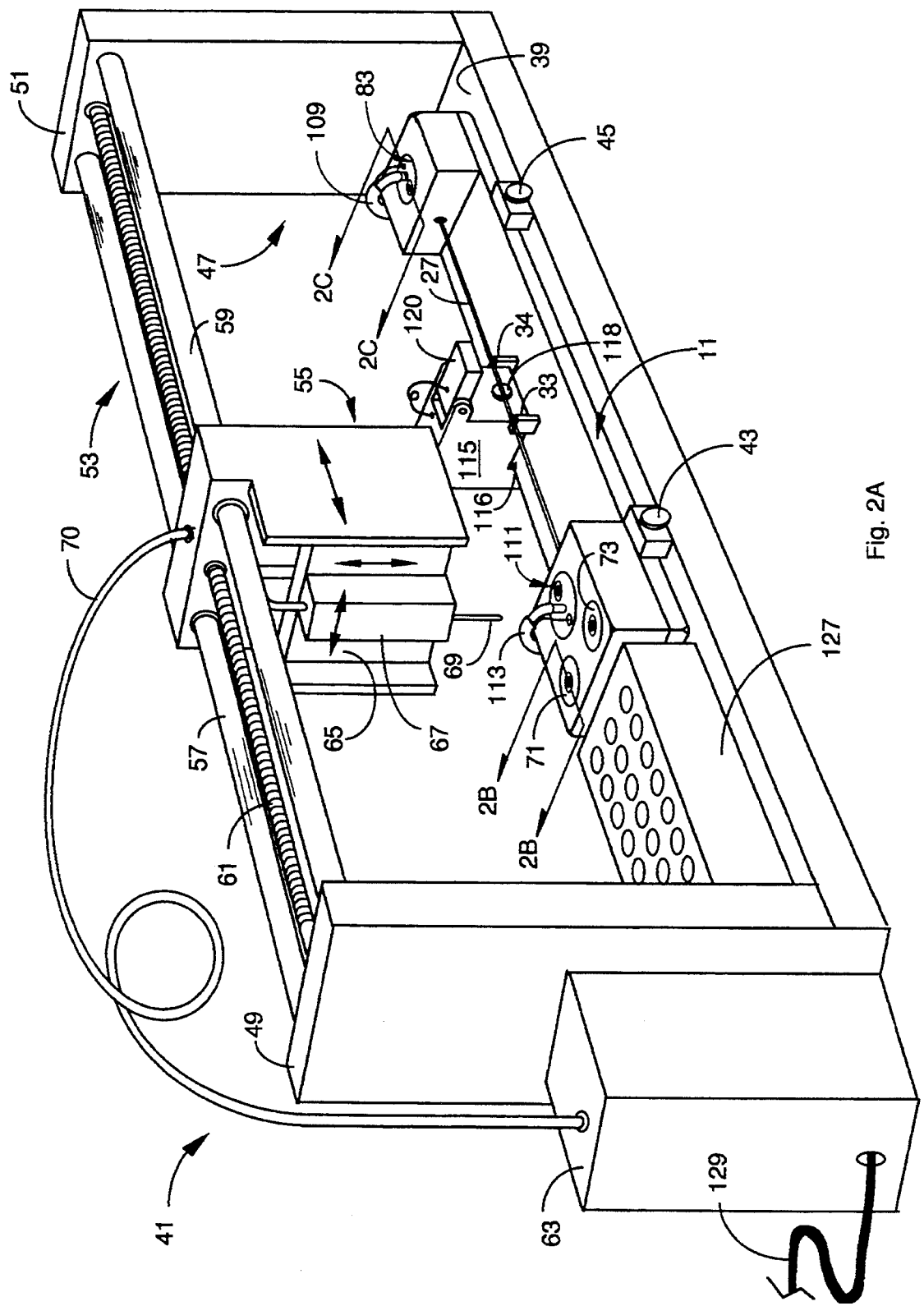
FIG. 2A is an isometric view of a serving apparatus according to the invention with an application-specific cassette mounted for operation.

FIG. 2A is an isometric view of an application-specific cassette 11 according to the invention mounted in a serving apparatus 41. Cassette 11 is registered to a surface 39 of serving apparatus 11 by virtue of engaging pins (not shown) extending from surface 39 by bores (not shown) provided for the registering purpose in the cassette. In this arrangement the cassette is held in place by screw clamps 43 and 45.

There are many alternative means of registering and holding the cassette in serving apparatus 41, and the means described is convenient, rather than required in the invention.

In the embodiment illustrated by FIG. 2A the serving apparatus comprises a frame 47 comprising end towers 49 and 51 rigidly connected to base 39 and supporting a carrier beam 53 positioned above the cassette and parallel to the long axis of the cassette. The carrier beam is for supporting and guiding a horizontal carriage 55 along the length of and above the cassette registered to surface 39.

In the embodiment shown in FIG. 2A carriage 55 is supported by linear bearings (not shown) on two precision shafts 57 and 59, and is translated by turning a worm shaft 61 that engages a precision worm nut (not shown) fixed in the carriage. The worm shaft is driven by a drive train powered by a stepper motor in an enclosure 63 at the end of the serving apparatus.

The linear drive is a precision drive capable of accurate positioning of the carriage along the length of carrier beam 53, and includes position sensors (not shown) for determining exact position for purposes of positioning the carriage and calibrating the translation apparatus.

Horizontal carriage 55 supports a vertical carriage 65 having drive means for limited vertical translation. Moreover, vertical carriage 65 carries a second horizontal carriage 67 that may be positioned in three horizontal positions along a horizontal axis at a right angle to the long axis of beam 53. Horizontal carriage 67 carries a demountable probe 69, which is in the nature of a hypodermic needle, and connects to a tubing leading to a syringe pump, described in more detail below.

When an application-specific cassette is mounted to the serving apparatus the sealing covers are removed and durable run covers are mounted to the openings of the buffer and storage reservoirs. For example, covers 71 and 73 are mounted to reservoirs 23 and 25, respectively.

Figure 2B:
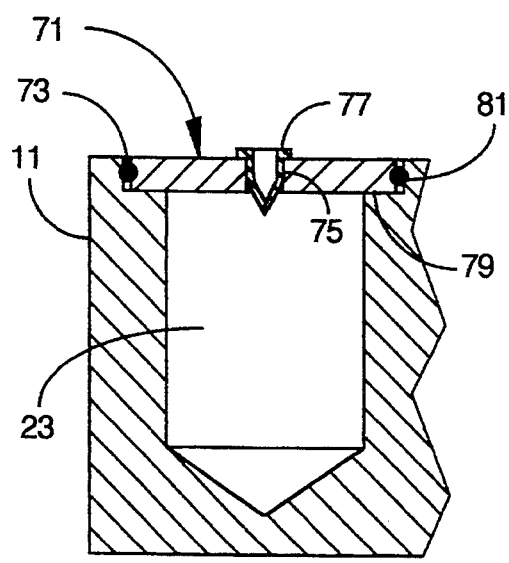
FIG. 2B is a cross section of a reservoir of a cassette along section line 2B—2B of FIG. 2A.

FIG. 2B is a partial cross-section through reservoir 23 and cover 71 along section line 2B—2B of FIG. 2A. In the present embodiment, cover 71 incorporates an o-ring 73 in a groove, and the cover engages in a counterbore 79 provided at the open end of the reservoir. An o-ring groove 81 is provided in the counterbore to receive the o-ring of the cover, so the two snap securely together in engagement.

A flexible pass-through 77 engages in a bore 75 at the center of the cover, providing a passage whereby probe 69 may enter and exit the reservoir without exposing the contents in the reservoir, and sustaining a low pressure seal, allowing procedures to be employed requiring positive pressure above atmospheric pressure in the reservoir. Typical procedures are described below, and require pressure differential generally on the order of 100 psi and lower. Pass-through 77 in the present embodiment is a radially symmetrical, conically shaped gasket, molded from one of several available flexible polymers, such as PVC.

Figure 2C:
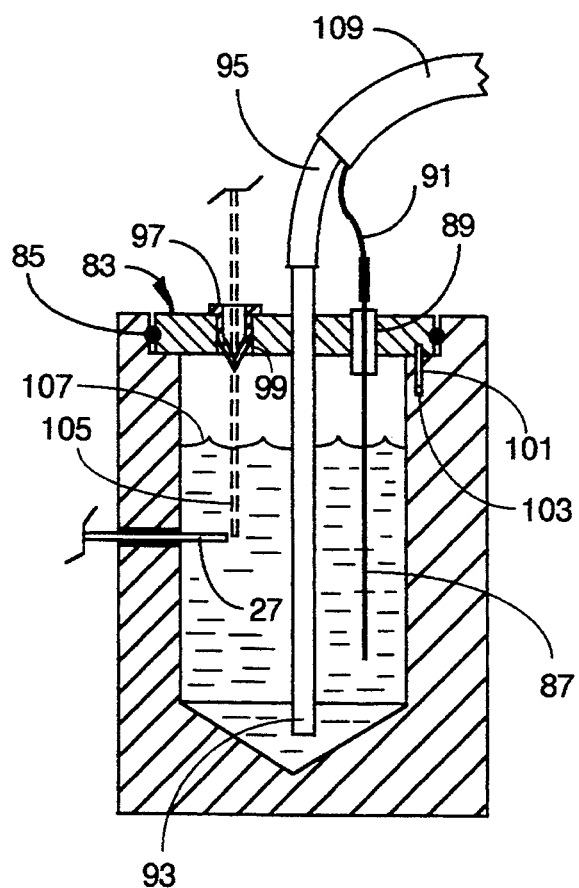
FIG. 2C is a cross section of a buffer reservoir of a cassette along section line 2C—2C of FIG. 2A.

FIG. 2C is a section taken along line 2C—2C through a cover assembly 83 assembled to buffer reservoir 19 in operation. Cover assembly 83 has an o-ring 85 mounted in a groove in the cover just as described above for cover 71, and the counterbore in the reservoir opening has a receiving groove for engaging the o-ring and providing a secure seal and maintaining the cover in place during use.

A platinum electrode 87 is mounted through a seal 89 in cover assembly 83 and provides a means of applying electrical potential to the run buffer in the buffer reservoir, as required for electrophoresis. The electrode is attached on the outside of the cover assembly to a high voltage line 91 leading away from the reservoir and eventually to a high-voltage power supply in enclosure 63 (FIG. 2A).

A waste tubing 93 is similarly sealed through the cover and attached to a flexible tubing 95 leading to a waste container or drain (not shown) away from the cassette. A pass-through 97 like pass-through 77 in FIG. 2B is engaged in a bore 99 through the cover assembly, and provides access for probe 69 (FIG. 2A) to the interior of the buffer reservoir.

For the buffer reservoir in the particular embodiment illustrated, the pass-through for the probe is off-center, and a locating pin 101 fixed in the cover assembly and engaging a bore 103 in the cassette determines the location of the pass-through in assembly. The cover and pin locations are configured to place the center of the pass-through above, in line with, and just beyond the end of capillary 27 in the buffer reservoir. Dotted outline 105 indicates the position of probe 69 inserted through pass-through 97 to the depth of the capillary beneath the surface 107 of run buffer in the buffer reservoir. It will be apparent to those with skill in the art that there are alternative means of locating the cover to the proper position.

The positioning of the probe relative to the capillary end is the reason for careful control of length D3 of the capillary and placement D2 of the capillary relative to the cassette (see FIG. 1B). As will be detailed below, transfer of sample material to be electrophoresed and fraction collection are dependent on this placement.

Waste tubing 95 and high voltage lead 91 in the present embodiment extend away from the reservoir cover within a common outer covering 109, which leads to enclosure 63.

A cover assembly 111 similar to cover assembly 83 assembles to the buffer reservoir 21 on the opposite end of cassette 11 from buffer reservoir 19. Cover assembly 111 is generally opposite hand from assembly 83, comprises a waste tube, a platinum electrode, and a pass-through for the probe, and places the pass through so probe 69 may be positioned at the end of the capillary in buffer reservoir 21 as well as in buffer reservoir 19. A high voltage wire for the electrode of cover assembly 111 leads away from cover assembly 111 along with a waste tube in a common cover 113. The electrode is powered by the high voltage supply in enclosure 63.

A detector cell assembly 115 mounted to the serving apparatus provides a means for detecting separated bands of materials passing through the capillary and passing the information to monitoring circuitry of a connected control system described more fully below. The detector cell assembly is mounted with a space 116 allowing the cassette to be inserted from the front such that capillary supports 33 and 34 span the width of the detector cell assembly providing an aid in placing and positioning the cassette.

When the cassette is registered in the serving assembly in the present embodiment, the capillary between supports 33 and 34 is positioned precisely against a detector beam focusing element 118. A detector unit incorporating light sensitive diodes is mounted in a pivotal element 120 that is pivoted up (as shown) for positioning a cassette in the serving apparatus, and down and latched (not shown) for operation, which places the detector assembly diodes in position to intercept light passed through or emitted from the capillary tubing. In a preferred embodiment the detector apparatus is that used in the Model 270 Electrophoresis apparatus marketed by Applied Biosystems of Foster City Calif.

It will be apparent to those with skill in the art that there are several alternatives in detection. Among them are electrochemical detection, UV absorbance, and fluorescent detection. Detectors of the different sorts may be adapted in the present invention.

In the presently described embodiment, referring to FIG. 2A, the translating carriages are in extent all within the outer boundaries defined by end towers 49 and 51. Although not shown, there are removable outer covers for enclosing the cassette, carriages, and other elements. Temperature control devices within enclosure 63 provide temperature management within the enclosure in operation, typically in a range of from 10 to 50 degrees C.

Figure 2D:
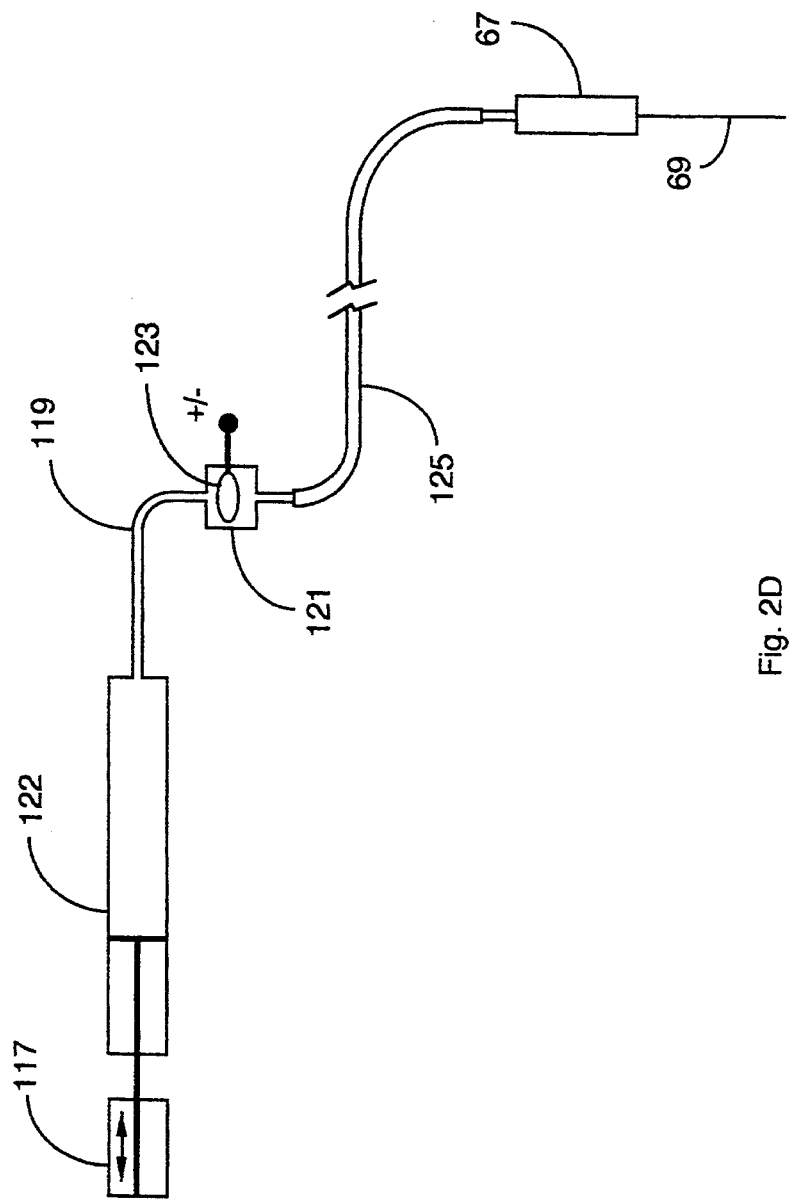
FIG. 2D is a mostly schematic illustration of a liquid-handling apparatus of a serving system according to the invention.

FIG. 2D is a mostly schematic diagram of some elements serving probe 69 in serving apparatus 41. A syringe pump 122 driven by a remotely controllable actuator 117 is connected by conduit 119 to an electrode housing tee 121 wherein an electrode 123 connected to a high voltage power source is capable of providing an electrical potential in liquid in the tee. The tee is connected to tubing 125 leading to probe 69. The syringe pump and actuator are located in enclosure 63 (FIG. 2A), and tee 121 with electrode 123 is located in the carriage assembly. A high voltage lead for the electrode passes through common bundle 70 along with tubing 119 leading from enclosure 69 to carriage 55 with sufficient slack to allow the carriage to travel to the full reaches of beam 53. Power and control lines for actuating mechanisms for the various motions of carriage 55 also pass through bundle 70.

The arrangement of the syringe pump, electrode 123, and probe 69 allows for a number of useful functions to be described more fully below.

Also registered to surface 39 of serving apparatus 41 is a supply block 127 providing multiple container positions arranged in three rows parallel to the long axis of cassette 11, such that the centerline of one row passes through the centerline of reservoir 23, the centerline of the center row passes through the centerlines of the inlet and outlet buffer reservoirs 19 and 21, and the centerline of the remaining row passes through the centerline of reservoir 25.

Supply block 127 provides a means of presenting samples to the system for separation, presenting fresh buffers without removing the cassette, and providing containers for fraction collection. Although not seen in FIG. 2A, there is also a wiper and waste tube outlet for the probe, and in some embodiments, a wash station may be incorporated.

The three directions of motion of the translation mechanisms integrated into serving apparatus 41 are capable of moving the tip of probe 69 into either of the inlet and outlet buffer reservoirs, either of auxiliary reservoirs 23 and 25, and into a container at any one of the container positions in auxiliary block 127.

In following descriptions translations of the probe tip will be referred to as X in the horizontal direction along the axis of the cassette, Y horizontal and at right angle to X, and Z as vertical translation.

Because of the registration of the cassette and the auxiliary block onto surface 39, there are a specific number of repeatable X-Y positions for the present embodiment. For example, carriage 55 must be able to travel to the X coordinate for each of the positions of auxiliary block 127, to the common X coordinate for reservoirs 23 and 25 in the cassette, and to the X coordinate for each of the inlet and outlet buffer reservoirs. In the embodiment shown this is ten X positions, but there may be more or fewer in other embodiments.

In the Y direction, the arrangement of all the elements is such that there are just three repeatable Y coordinates. This arrangement for X and Y positions provides a simplifying situation that allows sensors to be used for flagging X positions, and Y carriage 100 is actuated to a back position, a center position, and a forward position, which are fixed positions for the actuator.

In the Z direction for the probe (vertical) there needs to be an uppermost position at a height sufficient for probe 69 to clear all elements of the cassette and the auxiliary block and any containers, and at least one lower position wherein the tip of the probe is at the level of the end of the capillary in the cassette, which is a common height for each of the buffer reservoirs. It is useful as well to have at least one other vertical position to allow the probe to reach very near the bottom of the buffer reservoirs, and there may also be one or more different Z coordinates needed in using the probe in conjunction with the sample and fraction collection reservoirs, and with wash, wipe and waste stations if used.

There are then as many as five vertical positions to be repeated, and these are set as a function of adjustable sensors provided with the actuator for vertical carriage 65. In other embodiments there may be more or fewer than 5 vertical coordinates to be repeated.

Control of the serving apparatus in operation may be accomplished in several ways. In the apparatus shown an I/O interface and a microprocessor controller are built into the serving apparatus in enclosure 69, and a communication cable 129 leads to an LCD display and input interface (not shown). Through the interface an operator may enter pre-programmed sequences or series of sequences, and also may control the apparatus manually. Alternatively, cable 129 may be a serial communication cable connected to a general-purpose computer having a dedicated program for operating the apparatus. A power cable (not shown) connects also to enclosure 63 to furnish the power requirements.

The serving apparatus illustrated principally by FIG. 2A is but a single example of a serving apparatus that may be used with an application specific cassette according to the present invention. In an alternative embodiment a cassette is provided without the counterbores at the openings of the reservoirs, and covers are provided mounted on vertically traversing carriages with the serving apparatus, including o-ring seals for sealing to the top of the cassette around the reservoir openings.

In yet another alternative embodiment an X-Y-Z apparatus for moving the probe is used comprising stepper motor drives and a capacitance sensing means associated with the probe. An apparatus of this sort is disclosed in copending application Ser. No. 07/927,254, incorporated herein by reference. There are other such systems in the art that might be used with an application specific cassette, and it will be apparent to one with skill in the art that there are many ways that the requirements of the serving apparatus might be met. There are, indeed, commercial robotic devices known to the inventor which might well be adapted to function as the serving apparatus in the present invention.

Once an application-specific cassette according to the invention is fixed in position to a serving apparatus, the system comprising the cassette will perform a finite number of separations until buffer is depleted or capillary performance deteriorates. At this point the user may remove the used cassette and replace it with another for the same or for a different application.

Figure 3A:
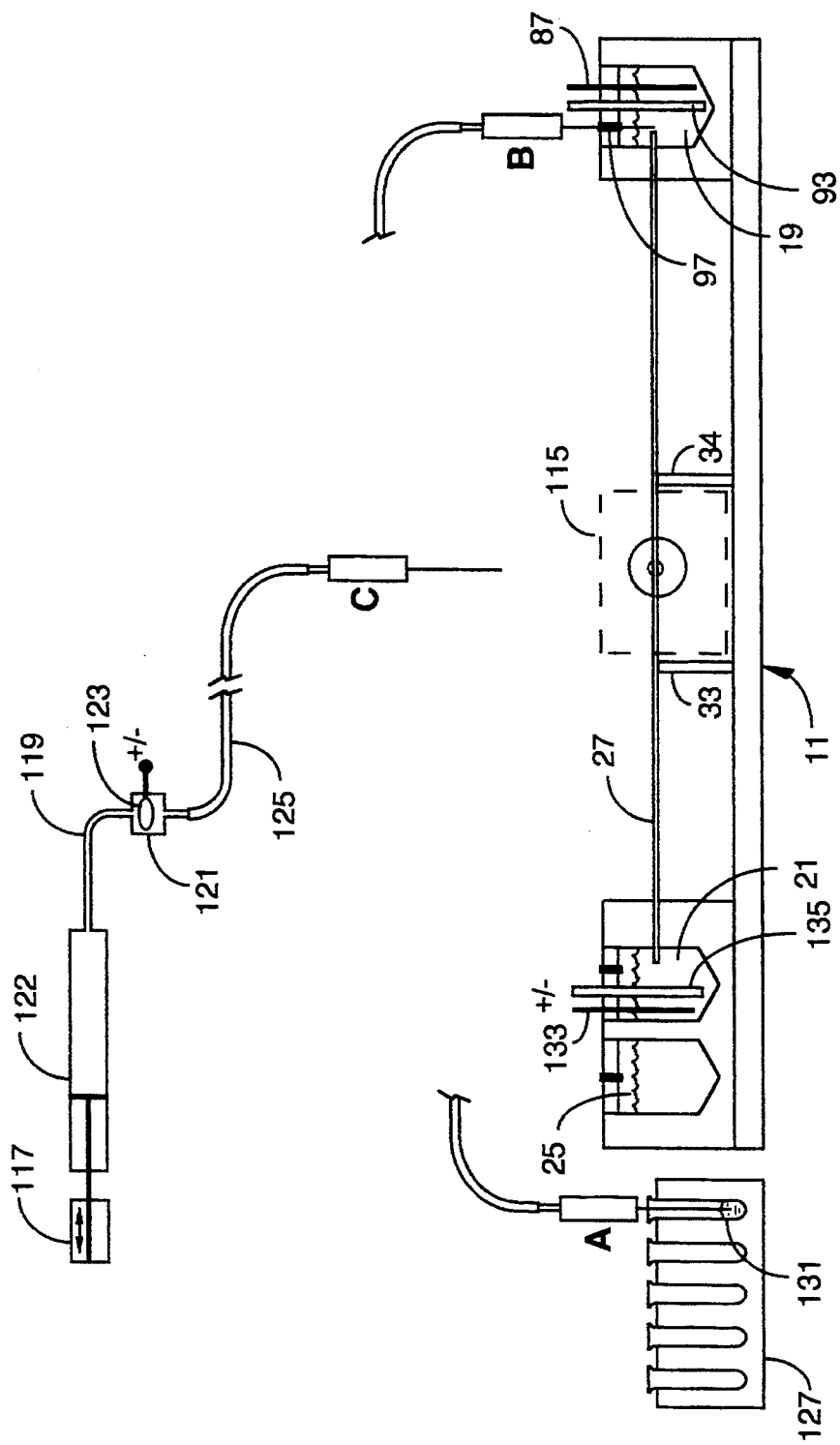
FIG. 3A is a schematic showing specific operations of the apparatus of the invention.

FIG. 3A is a partially schematic elevation view of cassette 11 and auxiliary block 127 with sample vials and fraction collection vials, such as vial 131, in auxiliary block 127 registered on surface 39, showing probe 69 in an idle position. Similar views are used below to illustrate various operations of the system. In FIG. 3A buffer reservoir 19 has waste tube 93, and an electrode 87. Buffer reservoir 21 has a similar waste tube 135 and electrode 133. Electrode 123 is resident in tee 121. It is important to the following operating descriptions that the three electrodes may be biased independently, and important too, to remember that, although only X and Z translations may be illustrated in the schematic of FIG. 3A and similar schematics, there is also a Y translation (into the plane of the paper in the figure) to reach more auxiliary and sample positions.

Figure 3B:
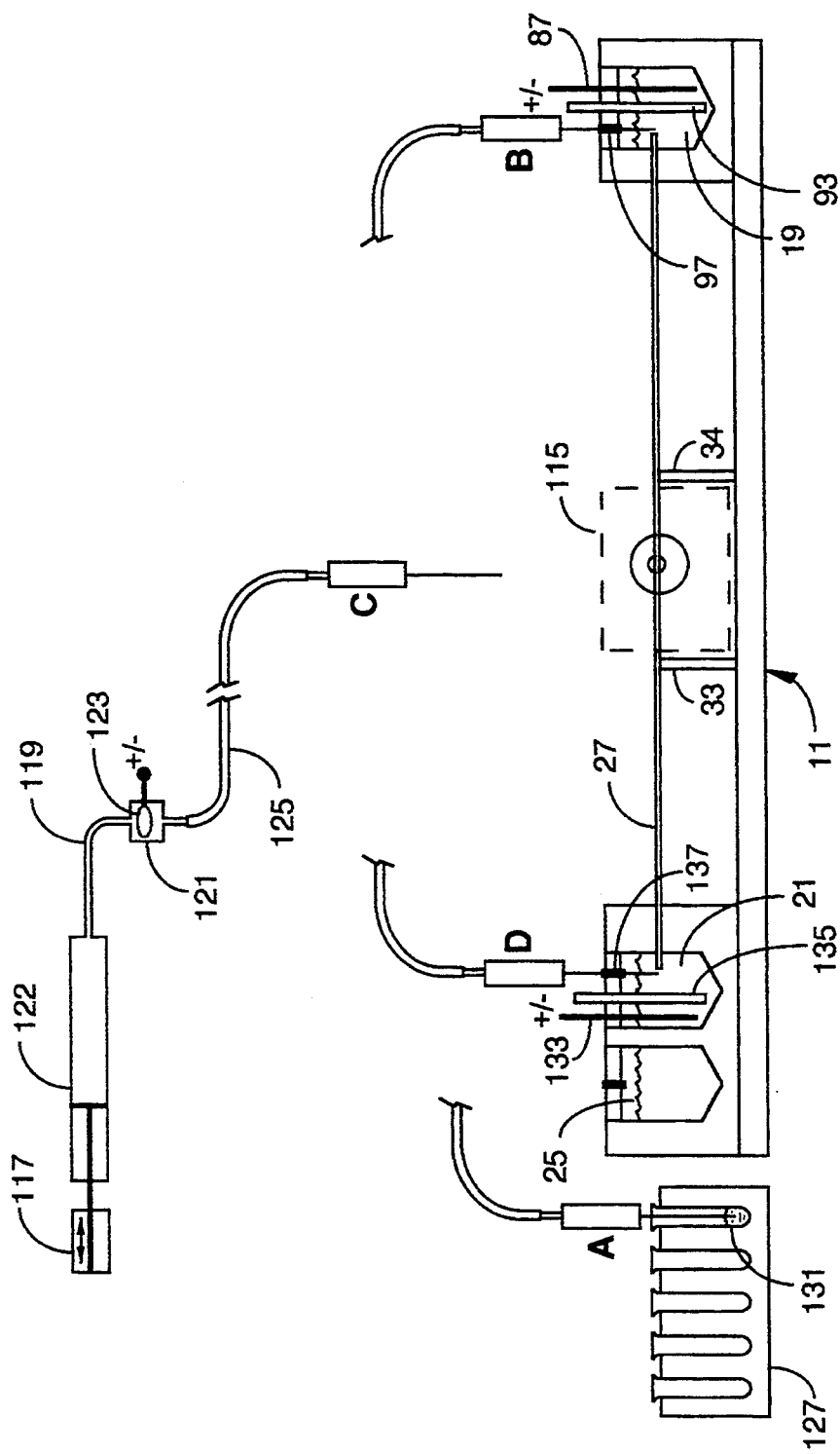
FIG. 3B is another schematic illustrating specific operations.

The operation of sample injection is illustrated in FIG. 3B. Probe 69 passes to a selected sample S in a vial 131 in block 127 (or in any other similar sample vial) shown as position A, by operation of the X-Y-Z translation subsystem. Probe 69 submerges in the sample, and by operation of syringe pump 122 withdrawing a finite amount, a volume of sample is withdrawn from the vial into the probe tip. The probe is then translated from the sample vial to the inlet buffer reservoir, which may be either of the buffer reservoirs. In this case, buffer reservoir 19 will be the inlet buffer reservoir.

The probe tip is lowered through pass-through 97 to a depth in the run buffer where the probe tip is immediately adjacent to the end of the capillary, as shown in position B. An electrical potential is now applied across electrodes 123 and 133, or 87 and 133, or both. The potential causes electromigration of charged analytes from the probe tip into the capillary. Selected operation of syringe pump 122 to expel sample at a predetermined rate, usually very slowly, may also be incorporated in some instances.

After sample injection, the electrical potential is removed, and the probe tip returned to idle position, shown as position C. Run potential is then applied across electrodes 87 and 133 causing charged analytes to migrate through the capillary, forming separated bands, past detector assembly 115, and eventually into outlet buffer reservoir 21.

Fraction collection may be accomplished by moving the probe tip during an electrophoresis run to the outlet buffer reservoir, in this case reservoir 21, and down through pass-through 137 to a position immediately adjacent to the outlet end of the capillary, similar to the position taken for sample injection in the inlet buffer reservoir. This position is shown as position D in FIG. 3B. At an appropriate time during a run, electrical potential across electrodes 87 and 133 is removed, and a potential is established across electrodes 123 and 133, causing analytes eluted from the end of capillary 27 to migrate into probe tip 69. Again, the process may in some instances be aided by selected operation of syringe pump 122.

After a fraction is collected from the capillary into the probe tip, the tip is removed from the outlet buffer reservoir, electrical potential re-established across 87 and 133 to continue the run, and the probe tip is translated to one or another of fraction collection vials in block 127.

When buffer depletion occurs before capillary deterioration, buffers may be replenished in the buffer reservoirs, either with the same, or with different buffer. The replenishment sequence is made possible by the ability of the seals and pass-throughs to countenance a positive pressure above atmospheric pressure.

Figure 3C:
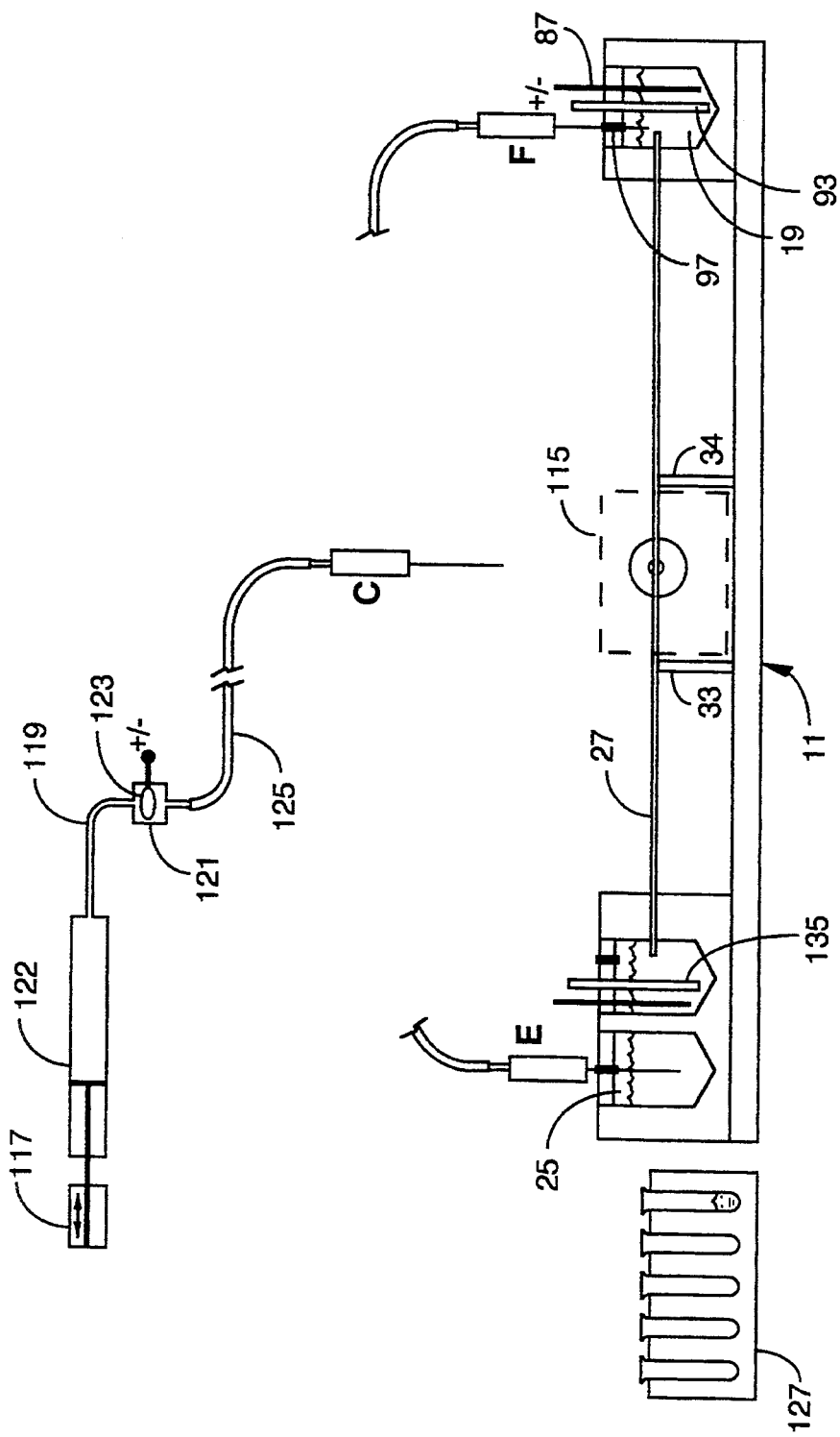
FIG. 3C is another schematic showing specific operations of the apparatus of the invention.

FIG. 3C shows the basics of buffer replenishment. Buffer reservoir 19 is used as illustrative. Probe 69 is first moved to a buffer storage reservoir, which in this example is reservoir 25 in the cassette. Buffer might also be stored at auxiliary positions in the serving apparatus reachable by the probe. The probe passes down through pass-through 139 below the surface of the buffer in the reservoir, and the syringe pump is operated to withdraw fresh buffer into the probe, lines 125 and 119, tee 121, and syringe pump 122, in sufficient quantity to replenish the buffer in reservoir 19. This position is shown in FIG. 3C as position E.

After taking up fresh buffer, the probe is moved to position F through pass-through 97 below the surface of buffer in the reservoir. Syringe pump 122 is then operated to expel the fresh buffer into the reservoir, forcing the depleted buffer out of the reservoir and to waste by means of waste tube 93 (connected to waste containers or drain).

For large-diameter open-tube capillaries, expulsion of fresh buffer from the probe into reservoir 19 might well result in buffer transfer through the capillary rather than to waste. For this reason valves are provided independently in waste lines 109 and 113 although the valves are not shown (see FIG. 2A). To avoid transfer through the capillary in the replenishment procedure described above, the valve in line 113 for waste tube 135 in reservoir 21 is closed, and the valve in line 109 for waste tube 93 in buffer reservoir 19 is open.

An open-tubed capillary may be flushed by a procedure similar to the buffer replenishment procedure. To flush capillary 27 from buffer reservoir 19 to buffer reservoir 21, the valve for waste tube 93 is closed and the valve for waste tube 135 is opened while buffer is injected into reservoir 19, Probe 69 may be rinsed between sampling, buffer replenishment or replacement, or other reagent use, by moving the probe to an auxiliary vial containing a rinse solution, drawing up a finite volume, moving the probe to an optional wash station, and expelling the rinse solution in a bore providing back-flow of the solution around the outside of the probe. An optional wipe station may also be employed.

By virtue of the translation ability of the serving apparatus a variety of sample preparation, buffer manipulation, and other procedures may be performed during and between electrophoresis runs. By transferring samples, buffers, diluents, or reagents from one vial to another, the system may accomplish dilutions, addition of reactants, sampling reactions at timed intervals, desalting of samples, and other chemistries requiring liquid transfers.

It is also within the scope of the invention to automate cassette replacement to the serving apparatus, so that cassettes may be automatically inserted, interfaced, and removed, permitting unattended operation of multiple and different applications.

Figure 4:
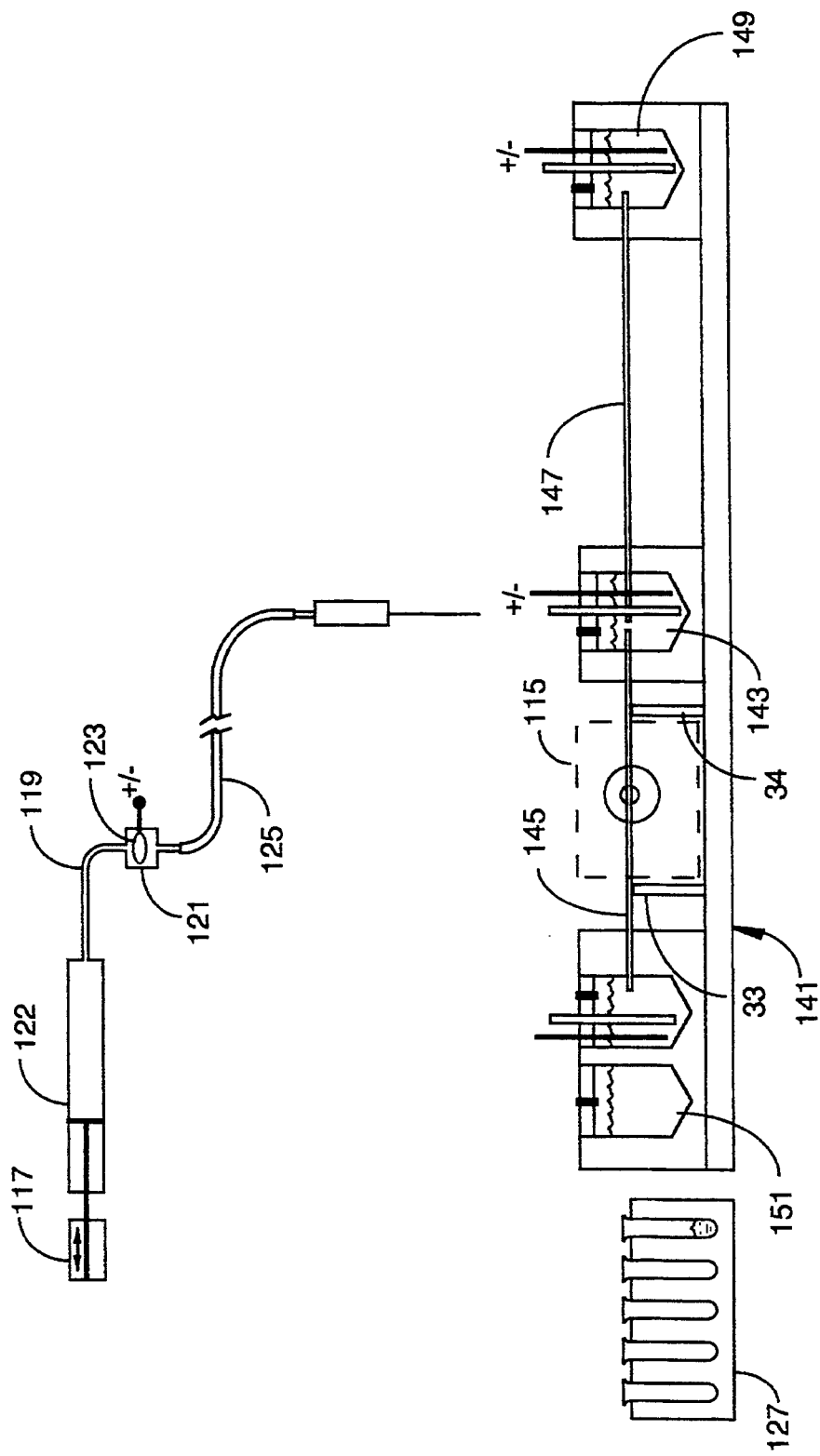
FIG. 4 is a cross section showing a cassette according to the invention having an intermediate reservoir for post separation detection.

FIG. 4 shows an embodiment of the invention useful for post-separation detection. In this embodiment a cassette 141 is provided with an intermediate reservoir 143 and two capillaries 145 and 147, and outboard buffer reservoirs 149 and 151. All three buffer reservoirs are provided in the serving apparatus with waste tubes, electrodes connected to high voltage sources, and pass-throughs for the probe to maintain pressure ability, as described above for the cassette with two buffer reservoirs.

In operation the probe would deliver a post-separation buffer or reactant to the reservoir in the manner described above for buffer replenishment. Separation is performed in a first capillary section, either capillary 145 or 147, separated analytes exit the first column (capillary), move across the gap between columns in the intermediate reservoir reacting with the buffer or reactant in the intermediate reservoir, enter the second capillary column, then move past detection cell 153 on the way to reservoir 151. All the other techniques described for the two reservoir cassette are available to be used with the three-reservoir cassette.

In the cassette aspect of the invention, there are specific combinations of separation matrices, buffer solutions, and the like that may be provided to accomplish specific types, kinds or classes of separations. Some examples are included here.

As one example, for the separation of SDS-denatured proteins the capillary of an application-specific cassette according to an embodiment of the invention contains a cross-linked, polymerized gel of acrylamide in a buffer. The gel is 5.1% total acrylamide and 2.6% bis-acrylamide crosslinker (i.e. 5.1% T and 2.6% C) in a buffer of 300mH Tris (pH 8.8), 3.2 mM sodium dodecylsulfate (SDS), and 2.3M ethylene glycol. The inlet and outlet buffer reservoirs contain the buffer only. The auxiliary reservoirs optionally contain the same buffer, allowing buffer to be replaced in operation until the separation matrix deteriorates, at which time the used cassette is removed and discarded and a new cassette containing the same materials is inserted in a serving apparatus.

As another example, for the separation of DNA sequencing products the capillary contains a cross-linked polymerized gel of acrylamide in a buffer. In this case the gel is 6% T and 5% C, 8% M urea, and a buffer of 89 mM Tris, 89 mM boric acid, and 2% mM EDTA at pH 8.3. The inlet and outlet buffer reservoirs contain the buffer solution but no gel. Again, the auxiliary reservoirs (if any) may contain additional buffer solution for replacing used solution as needed during operation, extending the useful life of a cassette.

There are many more examples known to the inventors and representing separation matrix and buffer solutions use for specific types of separations. The following list of references contains information presenting specific sets of variables for several more specific types of separations, but is not meant to be limiting, as there are many more such sets of circumstances, and new sets may be incorporated to application specific cassettes as they are discovered and developed.

For DNA restriction fragments and for polymerase chain reaction (POR) amplified products, see Heiger, D. N., *Journal Chromatography*, 516, 33 (1990). For DNA sequencing products see Swerdlow, H. et el., *Journal Chromatography*, 516, 61 (1990). For separation of synthetic single-stranded DNA, see D. Demorest et el., *Journal Chromatography*, 559, 43 (1991).

For SDS-proteins see Tsuji, K., *Journal Chromatography*, 550, 823 (1991). For native proteins see Cohen, A. S., et al., *Chromatograhia*, 24, 15 (1987). For oligosaccharides see Liu, J., et al., *Journal Chromatography*, 559, 223 (1991).

For materials for an application-specific cassette for separating DNA restriction fragments in an application having a liquid polymeric matrix (entangled polymer solution), where the matrix is the same in the column and in the reservoirs, see Chin, A.M., et al., *Am. Biotech. Lab./News Ed* 7 (10A), 16 (1989). For SDS proteins in a liquid polymeric matrix, see Widhalm, A., et al., *Journal Chromatography*, 549, 446 (1991).

It will be apparent to those with skill in the art that there are many changes that might be made without departing from the spirit and scope of the invention. Many variations have already been described above, such as material and construction variations for the cassette. There are even more variations that might be made in the serving apparatus. The level of automation is also a variable option, and a system according to the invention may be manually operated or fully automated.

What is claimed is:

1. An application-specific cassette for capillary electrophoresis comprising:
   a base for supporting and positioning elements of the cassette;
   an inlet buffer reservoir fastened to the base, said inlet buffer reservoir having a first upper opening and containing a first run buffer;
   an outlet buffer reservoir spaced apart from said inlet buffer reservoir and fastened to the base, said outlet buffer reservoir having a second upper opening and containing a second run buffer;
   a capillary electrophoresis column sealed through a sidewall of and opening at one end into said inlet buffer reservoir below the surface of said first run buffer, and sealing through a sidewall of and opening at the other end into said outlet buffer reservoir below the surface of said second run buffer, said capillary electrophoresis column having a separation matrix therein; and
   removable seals for sealing said first and second upper openings after placing buffer therein.

2. An application-specific cassette as in claim 1 wherein said inlet and outlet buffer reservoirs and said base are formed into a single injection molding.

3. An application-specific cassette as in claim 1 wherein said removable seals comprise one or more liquid-impervious films mounted to said upper openings by adhesive.

4. An application-specific cassette as in claim 1 comprising one or more auxiliary reservoirs each containing a chemical solution for use in an electrophoresis procedure, and sealable by a liquid-impervious film with an adhesive.

5. An application-specific cassette as in claim 1 wherein said inlet and said outlet buffer reservoirs are configured to engage cover assemblies at said upper openings, said assemblies for providing an electrode and a waste tube in the covered reservoir, the engagement of one of the cover assemblies at an upper opening being capable of sustaining a positive pressure above atmospheric pressure across the cover assembly.

6. A serving apparatus for receiving and using an application-specific cassette having an inlet and an outlet buffer reservoir, run buffers therein, and a capillary column, said serving apparatus comprising:
   a probe apparatus including a probe tip and a pump for aspirating and dispensing liquids to and from the buffer reservoirs and containers, said probe apparatus comprising a first electrode placed to contact liquid within said probe apparatus;
   translation apparatus supporting said probe apparatus for translating said probe apparatus in three dimensions;
   a first removable cover assembly configured for covering said inlet buffer reservoir and immersing a first waste tube and a second electrode in buffer solution therein, and providing an ability to support a positive pressure across said first cover assembly;
   a second removable cover assembly for covering said outlet buffer reservoir and immersing a second waste tube and a third electrode in buffer solution therein, and providing an ability to support a positive pressure across said second cover assembly; and
   a high voltage power supply connected to said first, second, and third electrodes for supplying electrical potential selectively and independently to each;
   said serving apparatus configured to accept and hold said application-specific cassette with said inlet and outlet buffer reservoirs within the translation range of said translation means.

7. A serving apparatus as in claim 6 wherein said pump comprises a syringe cylinder driven by a linear actuator.

8. A serving apparatus as in claim 6 wherein said first and second removable cover assemblies comprise pass-through seals for passing said probe tip within said inlet and outlet buffer reservoirs while maintaining ability of said cover assemblies to support a positive pressure differential across said removable cover assemblies.

9. A serving apparatus as in claim 6 further comprising auxiliary vials and containers of fluids within the range of said translation means.

10. A serving apparatus as in claim 6 further comprising a temperature controllable enclosure for enclosing said application-specific cassette when mounted in said serving apparatus to control the temperature of said capillary column.

11. A serving apparatus as in claim 6 further comprising a microprocessor-based control system for managing operations of said serving apparatus, said control system comprising an operator interface for entering commands and data.

12. A system for performing capillary electrophoresis comprising:
   an application-specific cassette having spaced-apart reservoirs fastened to and spaced apart on a base and containing run buffers, and a capillary column opening below the surface of said run buffers; and
   a serving apparatus configured to mount said application-specific cassette, said serving apparatus having a liquid transfer apparatus for presenting and withdrawing same materials and chemical solutions to and from said cassette, a first electrode placed to contact liquid within said liquid transfer means, a second electrode immersible in one of said buffer reservoirs and a third electrode immersible in the other, and a high voltage power supply connected to said first, second, and third electrodes for supplying electrical potential selectively and independently to each.

13. A system for capillary electrophoresis as in claim 12 wherein said application-specific cassette before mounting comprises removable seals for closing an upper opening of each of said buffer reservoirs, sealing said run buffers therein until ready for mounting to said serving apparatus.

14. A system for capillary electrophoresis as in claim 13 wherein said removable seals comprise liquid impervious film mounted to said upper openings by an adhesive.

15. A system for capillary electrophoresis as in claim 12 wherein said spaced-apart reservoirs each have an upper opening configured to engage a cover assembly in a manner to sustain a positive pressure differential across the cover assembly.

16. A system for capillary electrophoresis as in claim 12 comprising auxiliary vials and reservoirs, wherein said liquid transfer apparatus comprises a probe with a probe tip connected by fluid conduit to a syringe pump activated by a linear actuator, and translation apparatus for translating said probe tip in three dimensions to reach into said buffer reservoirs and said auxiliary vials and reservoirs.

17. A system for capillary electrophoresis as in claim 16 wherein said serving apparatus comprises cover assemblies each with a cover for closing upper openings in said buffer reservoirs, said cover assemblies each comprising an electrode sealed through the cover, a waste tube sealed through the cover, and a pass-through for passing a probe of said liquid transfer apparatus into the covered buffer reservoir, while maintaining an ability to sustain a positive pressure differential across the cover.

18. A system for capillary electrophoresis as in claim 12 further comprising a temperature controllable enclosure for enclosing said application-specific cassette.

19. An application-specific cassette for a specific capillary electrophoresis procedure involving post-separation detection comprising:
- an inlet buffer reservoir with a first upper opening and a first run buffer therein;
- an intermediate buffer reservoir spaced apart from said inlet buffer reservoir with a second upper opening and a post separation buffer therein;
- an outlet buffer reservoir spaced apart from said intermediate buffer reservoir, with a third upper opening and having a second run buffer therein;
- a first capillary electrophoresis column opening at one end into said inlet buffer reservoir below the surface of said first run buffer and opening at the other end into said intermediate buffer reservoir, said capillary electrophoresis column having a separation matrix therein;
- a second capillary electrophoresis column opening at one end into said outlet buffer reservoir below the surface of said second run buffer and opening at the other end into said intermediate buffer reservoir, said capillary electrophoresis column having a separation matrix therein; and
- removable seal means for sealing said first, second and intermediate upper openings after placing buffer therein.

* * * * *